July 3, 1956 R. E. SHEPHERD Plant Pat. 1,495
ROSE PLANT
Filed Oct. 25, 1955
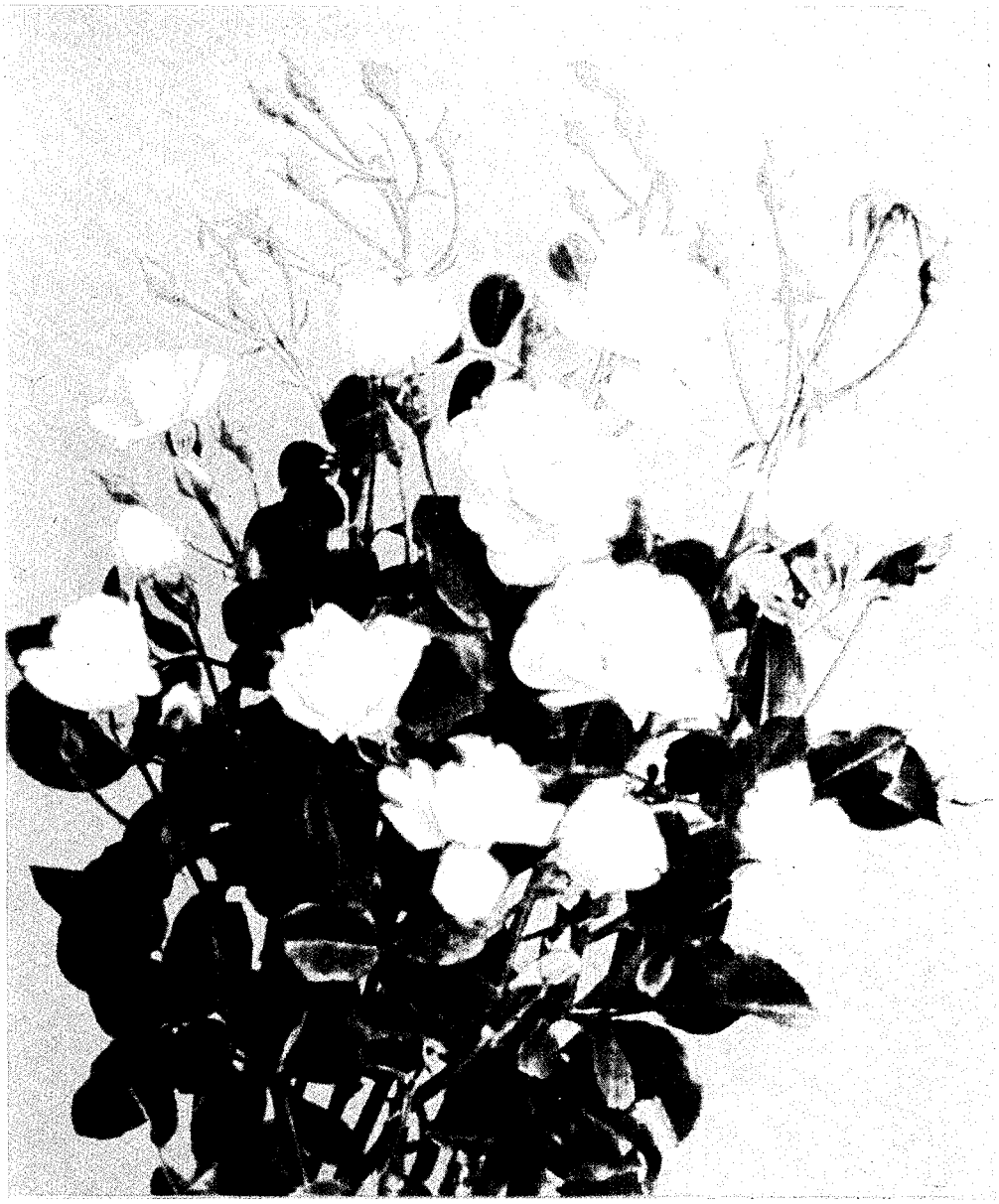
INVENTOR
Roy E. Shepherd
By Orville M. Kile
Plant Pat. Agent.

United States Patent Office

Plant Pat. 1,495
Patented July 3, 1956

1,495

ROSE PLANT

Roy E. Shepherd, Medina, Ohio, assignor to Edith C. Bosley, Mentor, Ohio

Application October 25, 1955, Serial No. 542,796

1 Claim. (Cl. 47—61)

My present invention relates to an improved variety of polyantha rose plant in the class having essentially white flowers. It was developed through a cross made by me at my greenhouse, between the variety Cecile Brunner (unpatented) and an unnamed seedling which had been a cross between R. Souileana and Mrs. Jos. Hiess (both unpatented).

This new variety has been asexually reproduced by me at Medina, Ohio, by means of budding, and its characteristics appear to be permanently fixed.

The accompanying illustration shows a bunch of several clusters of flowers of my new variety, indicating the large number of blooms and abundance of foliage as well as the delicate tinting on the essentially white blooms.

In the following detailed description, color plate numbers refer to Ridgway's Color Standards and Nomenclature, other color terms indicating the ordinary dictionary meaning.

THE PLANT

Growth habit: Upright, compact and bushy.

Flowering habit: Produces large loose sprays or panicles of flowers; abundant bloomer throughout the season.

Disease resistance: The variety is particularly disease-resistant and has proved to be nearly 100 percent black-spot-proof in Ohio even when grown alongside such Pernetiana types as Angels Mateau and Bright Wings, which had this disease at the time.

Stems: Strong although slender. Zigzag form, with relatively short internodes. Deep Dull Yellow Green (Pl. XXXII).

Foliage:

*Type.*—Pinnately compound, usually with 5 to 7 leaflets.

*Quantity.*—Abundant.

*Size.*—Medium, terminal leaflet measuring 1¾ by 1¼ inches.

*Shape.*—Oval, with acuminate point. Edge finely serrated.

*Texture.*—Leathery.

*Color.*—Upper surface approximately Empire Green (Pl. XXXII), highlighted with Deep Dull Yellow-Green (Pl. XXII). Under surface approximately Varley's Green (Pl. XVIII).

*Rachis.*—Grooved above, sometimes reddish tinged. Small thorns or prickles on under side.

*Stipules.*—Narrow; small points.

THE FLOWER

Bud:

*Size.*—Very small before calyx breaks.

*Form.*—Ovoid.

*Color.*—As calyx breaks, Reed Yellow (Pl. XXX) with base of Cartridge Buff (Pl. XXX). As first petal breaks, Pale Viridine Yellow (Pl. V) at base, blending to almost white at tip.

*Calyx.*—Comparatively large; hairy; Parrot Green (Pl. VI); purplish tinged on inner surface when reflexed.

*Sepals.*—Broad; simple; reflex early.

*Peduncle.*—Short; slender; stiff; beset with small prickles.

Bloom:

*Borne.*—In large irregular, branching clusters or panicles.

*Size.*—Small. Average about 1½ to 2 inches across.

*Form.*—High-centered at first, much like hybrid tea blooms. Later open into loose, informal, fluffy arrangement.

*Color.*—Opening flower is white with Light Viridine Green (Pl. VI) at its base on the outside, and Light Green-Yellow (Pl. V) on the inside. In the open flower the petals are essentially white with Chartreuse Yellow to Crysolite Green (Pl. XXXI) at the base and Seafoam Green (Pl. XXXI) in its depths. During the fall months a few of the center petals have a faint tinge of Shrimp Pink (Pl. I).

Petalage: Double. 70 to 80 petals, including petaloids.

Petals:

*Size.*—Small.

*Shape.*—Almost round. Edge whole except for notch at tip of most petals.

*Texture.*—Delicate.

*Fragrance.*—Slightly fragrant.

*Longevity.*—Long-lasting on bush and after being cut.

Reproductive organs: A green, leaflet-like growth is found in the center of the flower instead of pistils and stamens.

Having thus disclosed my invention, I claim:

The new and distinct variety of polyantha rose plant, substantially as herein shown and described, characterized particularly by its very vigorous and compact growth; its great resistance to blackspot; and its essentially white flowers of pleasing form as described.

No references cited.